United States Patent
Tochino et al.

(10) Patent No.: US 8,531,663 B1
(45) Date of Patent: Sep. 10, 2013

(54) PARTICLE DIAMETER DISTRIBUTION MEASUREMENT DEVICE

(71) Applicant: Horiba, Ltd., Kyoto (JP)

(72) Inventors: Shigemi Tochino, Kyoto (JP); Hiroyoshi Sawa, Kyoto (JP)

(73) Assignee: Horiba, Ltd. (JP)

( * ) Notice: Subject to any disclaimer, the term of this patent is extended or adjusted under 35 U.S.C. 154(b) by 0 days.

(21) Appl. No.: 13/768,023

(22) Filed: Feb. 15, 2013

(30) Foreign Application Priority Data

Feb. 16, 2012 (JP) ................. 2012-032162

(51) Int. Cl.
*G01N 15/02* (2006.01)
(52) U.S. Cl.
USPC ............................. 356/336; 702/29; 708/426
(58) Field of Classification Search
USPC .............. 356/335–343, 72–71; 702/29, 179; 708/191, 426, 801, 425
See application file for complete search history.

(56) References Cited

U.S. PATENT DOCUMENTS

| | | | | |
|---|---|---|---|---|
| 4,938,592 A | * | 7/1990 | Poole et al. .................... | 356/335 |
| 5,005,144 A | * | 4/1991 | Nakajima et al. ............... | 702/45 |
| 5,296,910 A | * | 3/1994 | Cole ............................ | 356/28.5 |
| 5,627,642 A | * | 5/1997 | Dhadwal et al. .............. | 356/336 |
| 6,191,853 B1 | * | 2/2001 | Yamaguchi et al. ........... | 356/336 |
| 6,885,448 B2 | * | 4/2005 | Tsutsui et al. ................. | 356/336 |
| 7,724,369 B2 | * | 5/2010 | Yamaguchi et al. ........... | 356/336 |
| 2011/0181869 A1 | * | 7/2011 | Yamaguchi et al. ............ | 356/72 |

FOREIGN PATENT DOCUMENTS

| | | |
|---|---|---|
| EP | 2093558 A2 | 8/2009 |
| GB | 2226129 A | 6/1990 |
| JP | 3645758 B2 | 5/2005 |
| JP | 2005-249759 A | 9/2005 |

OTHER PUBLICATIONS

Search Report under section 17(5) for U.K. patent application No. 1302605.9 dated May 8, 2103.

* cited by examiner

*Primary Examiner* — Sang Nguyen
(74) *Attorney, Agent, or Firm* — Cantor Colburn LLP

(57) ABSTRACT

A dynamic scattering type particle diameter distribution measurement device comprising a light receiving part that receives scattered light emitted from the particle group and that outputs a pulse signal in accordance with a photon number of the received light, a plurality of multibit counters that receives the pulse signal while a gate is open and counts a pulse number, a correlator that obtains auto-correlation data from time series data of the pulse number, and a calculation part that calculates particle diameter distribution based on the auto-correlation data, a gate time changing part that changes gate time once or a plurality of times and a gate time judging part that compares mutually the differences between the maximum value and the minimum value of the auto-correlation data output every time the gate time is changed and judges the gate time corresponding to the maximum difference as a recommended value.

3 Claims, 6 Drawing Sheets

PARTICLE DIAMETER DISTRIBUTION MEASUREMENT DEVICE

CROSS REFERENCE TO RELATED APPLICATIONS

Priority under 35 U.S.C. §119(a) is claimed from Japanese Application No. 2012-032162, filed 16 Feb. 2012, the disclosure of which is also incorporated herein by reference.

FIELD OF THE ART

This invention relates to a particle diameter distribution measurement device by means of a photon correlation method based on a dynamic scattering theory.

BACKGROUND ART

In accordance with the recent development of nanotechnology, a demand is growing for an extremely micro particle (hereinafter called as a single nanoparticle) of a single nanometer (1~10 nm). In case of manufacturing the single nanoparticle with high accuracy, since a grinding method has limitations, a method for producing a single nanoparticle by growing a crystal has been developing recently. In this case, it is necessary to measure a diameter of a particle during a process of growing the crystal in real time in order to control, for example, a particle diameter.

As a method for measuring a diameter of a particle among analyzing particles known are various methods such as a laser diffraction method and a centrifugal sedimentation method, however, practically from a view point of a performance and a cost, a photon correlation method that is based on a dynamic scattering theory is one of the most effective methods in order to measure a diameter of a single nanoparticle.

A particle diameter distribution measurement device as being a particle analytical device by the use of the photon correlation method based on the dynamic scattering theory irradiates the laser light on particles that are making the Brownian motion in a sample solution, receives the scattered light due to the particle by the use of a photoelectron multiplier, makes auto-correlation data based on a pulse obtained by shaping a waveform of an electric current signal output by the photoelectron multiplier and calculates particle diameter distribution of a particle group based on the auto-correlation data.

For example, in accordance with the device described in the patent document 1, in order to improve the accuracy of calculating the particle diameter distribution, the detected signal from the detector of the scattered light is processed to be an intermediate function, and the particle diameter distribution is calculated by conducting an inverse operation on the intermediate function, the data used for the inverse operation is extracted at appropriate intervals from all of the data area and a data table is made, furthermore an absolute value of first-order differentiation of the intermediate function is calculated. Then the bigger the absolute value is, the shorter interval the data is extracted at.

In accordance with the device described in the patent document 1, even though a big diameter particle exists, there might be a case that the data relating to the big diameter particle is extracted. In case that the data of the particle whose particle diameter is big is included, there might be a case that the accuracy of calculating the particle diameter distribution is degraded because of depending on the data of the particle whose diameter is big.

For the particle diameter distribution measurement device wherein the correlator or the counter is of a linear sampling method, the pulse number obtained by processing the electric current signal output from the photoelectron multiplier as being a detector of the scattered light is counted based on the pulse number received by the multiple multibit counters each of which has the gate and that are arranged in parallel in a state that the gate is open. Ordinarily, the time period while the gate of the multibit counter is open (hereinafter called as the gate time) is set by trial and error by a user of the particle diameter distribution measurement device prior to an actual measurement of the sample. Namely, the user repeats the measurement of the particle diameter distribution while changing the gate time, reviews the auto-correlation function obtained by the result of the measurement for every changed gate time and sets the optimum gate time based on the result. As a result of this, it might happen that is not necessarily the optimum setting. In addition, it takes time and labor prior to setting the gate time.

PRIOR ART DOCUMENT

Patent Document

Patent document 1: Japanese Patent Application Publication No. 3645758

DISCLOSURE OF THE INVENTION

Problems to be Solved by the Invention

The present claimed invention intends to solve all of the problems and a main object of this invention is to make it possible to avoid damage of the particle analytical device that analyzes physicality of a particle based on scattered light due to the particle by irradiating light such as laser and to restart the analysis rapidly in case that abnormal occurs in the scattered light.

Means to Solve the Problems

More specifically, a particle diameter distribution measurement device in accordance with this invention comprises a light irradiation part that irradiates light on a particle group that moves in a disperse medium, a light receiving part that receives scattered light emitted from the particle group on which the light is irradiated and that outputs a pulse signal in accordance with a photon number of the received light, a plurality of multibit counters that are arranged in parallel and each of which has a gate and receives the pulse signal while the gate is open and counts a pulse number, a correlator that obtains auto-correlation data from time series data of the pulse number obtained sequentially from each of the multibit counters, and a calculation part that calculates particle diameter distribution of the particle group based on the auto-correlation data obtained from the correlator, and is characterized by further comprising a gate time changing part that changes gate time once or a plurality of times and a gate time judging part that compares mutually, at every time when the gate time is changed, difference between the maximum value and the minimum value of the auto-correlation data output by the correlator at every time when the gate time is changed by the gate time changing part and judges the gate time corresponding to the maximum difference as a recommended value.

In accordance with this arrangement, it is possible to set the gate time appropriate for the sample by considering the change (attenuation) of the auto-correlation data by judging the gate time at a time when the difference between the maximum value and the minimum value of the auto-correlation data is output by the correlator.

In order to automate setting the gate time, it is preferable to further comprise a gate time setting part that sets the gate time judged by the gate time judging part to the multibit counter.

Effect of the Invention

In accordance with this invention, the gate time of the counter can be set easily tailored to the sample so that it is possible to reduce the time and labor required until the measurement of the sample.

BEST MODES OF EMBODYING THE INVENTION

One embodiment of this invention will be explained with reference to drawings.

A particle diameter distribution measurement device 1 in accordance with this embodiment gradually grows particles, is used together with a micro particle producing device (not shown in drawings) that produces single nano particles, and is utilized for measuring a particle diameter distribution and for controlling the particle diameter during a process of growing the particles.

Figure 1:
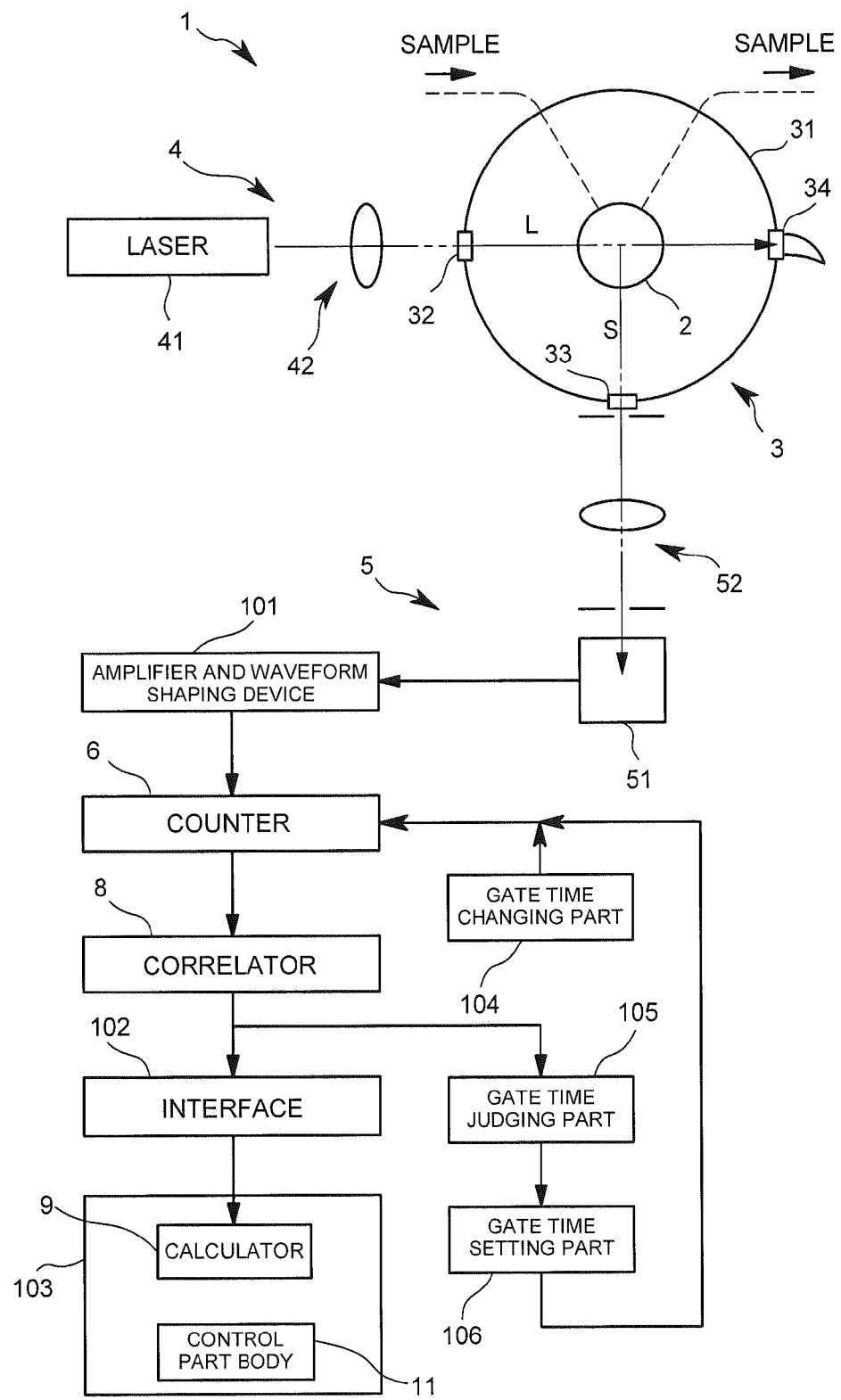
FIG. 1 is a pattern overall view showing a particle diameter distribution measurement device in accordance with one embodiment of this invention.

First, a fundamental configuration of this particle diameter distribution measurement device 1 will be explained. The particle diameter distribution measurement device 1 comprises, as shown in FIG. 1, a transparent cell 2 that houses a sample wherein a particle group is diffused in a dispersion media such as water, a bus 3 inside of which the cell 2 is oil-immersed, a light irradiation part 4 that irradiates laser light (L) on the sample through the bus 3 from outside of the cell 2, a light receiving part 5 that receives the scattered light (S) emitted from the particle group on which the laser light (L) is irradiated and that outputs an electric current signal in accordance with a photon number, a plurality of counters 6 that receive a pulse signal while the gate is open and count a pulse number of the pulse signal, a control part 7 that sets a period of time (hereinafter called as a gate time) when the gate of each counter 6 is open to be identical each other and that gives the timing when the gate opens to each counter 6 so as to be untimely, a correlator 8 that produces auto-correlation data based on time series data of the pulse number obtained by each counter 6, and a calculating part 9 that calculates particle diameter distribution of the particle group based on the auto-correlation data obtained by the correlator 8.

Each part will be explained.

The cell 2 is of a flow cell type that is hollow made of a transparent wall, and inside of which the sample flows unidirectionally at a pace within a predetermined speed. The sample is sent from the above-mentioned micro particle producing device, introduced into inside of the cell 2 through an introducing port and then discharged through a discharging port.

The bus 3 is made of a hollow wall body 31 that can be sealed and a transparent liquid having a refraction factor identical to or approximate to that of the cell 2 that is filled inside of the wall body 31, and the cell 2 is housed at a center of inside of the bus 3. The wall body 31 is made of, for example, an opaque metal and a laser light window 32 and a scattered light window 33 in order to transmit the light are arranged on an optical path of the laser light (L) and an optical path of the scattered light (S) respectively. A code 34 arranged on the wall body 31 opposite to the laser light window 32 is a light stopper to restrain the reflection by attenuating the laser light (L) passing the cell 2. In this embodiment, the optical path of the laser light (L) does not coincide with the optical path of the scattered light (S) (each optical path is orthogonal in FIG. 1), however, each optical path may coincide each other.

The light irradiation part 4 comprises, for example, a semiconductor laser 41 as being a light source, and a laser light guide mechanism 42 that condenses the laser light (L) irradiated from the semiconductor laser 41 on a light irradiation area (for example, a center) locating inside of the cell 2 through the laser light window 32. The laser light guide mechanism 42 consists of, for example, a light condensing lens or the like.

The light receiving part 5 comprises a photoelectron multiplier (PMT) 51 as being a light detector, a scattered light guide mechanism 52 that introduces the scattered light (S) passing the scattered light window 33 into the photoelectron multiplier 51, and an amplifier and a waveform shaping device 101 that transform an electric current signal output from the photoelectron multiplier 51 into a pulse signal. The photoelectron multiplier 51 outputs the electric current signal in accordance with a photon number of the incident light. The scattered light guide mechanism 52 is a mechanism wherein a lens is arranged between a pair of pinholes. The amplifier and the waveform shaping device 101 amplify a faint electric current signal output from the photoelectron multiplier 51 and transform the amplified electric current signal into a pulse signal that rises at the timing when the amplified electric current signal rises by shaping the waveform.

Figure 2:
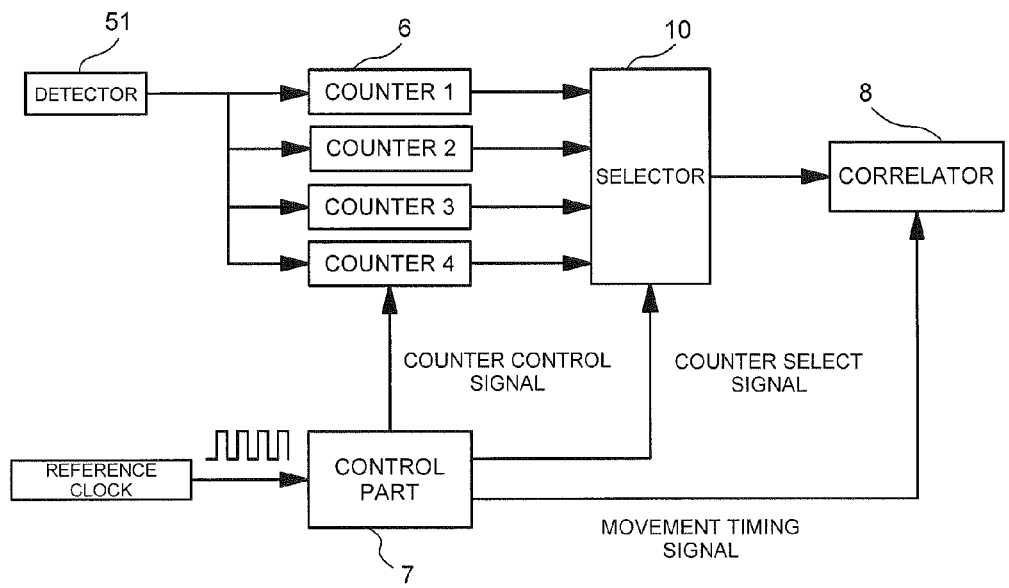
FIG. 2 is a hardware configuration view showing a hardware configuration in accordance with this embodiment.
Figure 3:
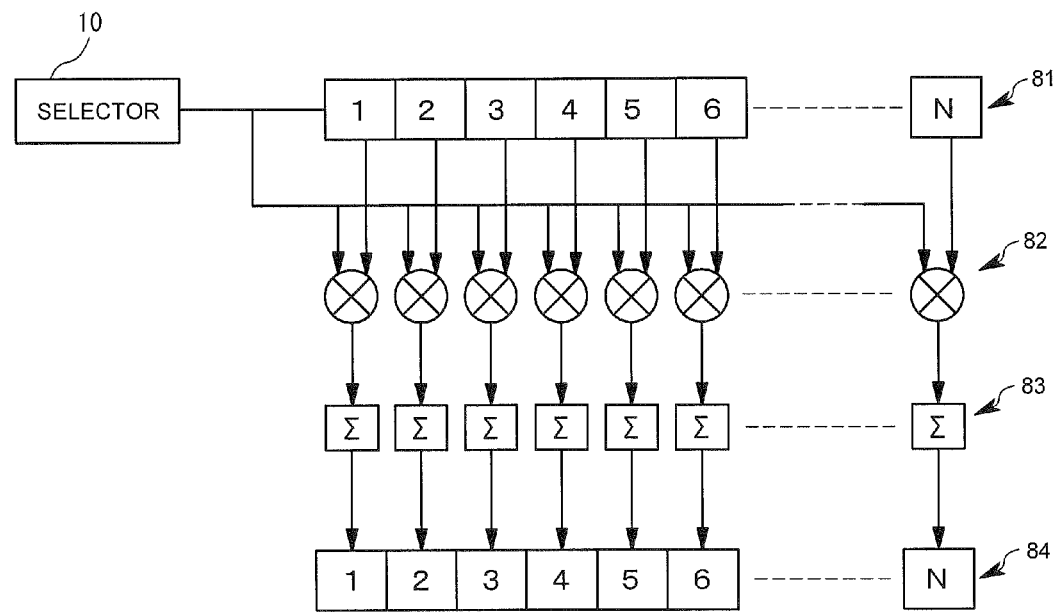
FIG. 3 is a hardware configuration view showing the hardware configuration in accordance with this embodiment.

The pulse signal output from the light receiving part 5 is, as shown in FIG. 2 and FIG. 3 in detail, input to a plurality (four, in this embodiment) of multibit (for example, 8 bits) counters 6 that are arranged in parallel. A gate (not shown in drawings) is provided for each of the counters 6, and the pulse signal is received and a pulse number is counted in a state that the gate is open. The timing (hereinafter called as the gate timing) of opening the gate and a time period while the gate is open, namely the gate time are controlled by a counter control signal sent by the control part 7.

Figure 4:
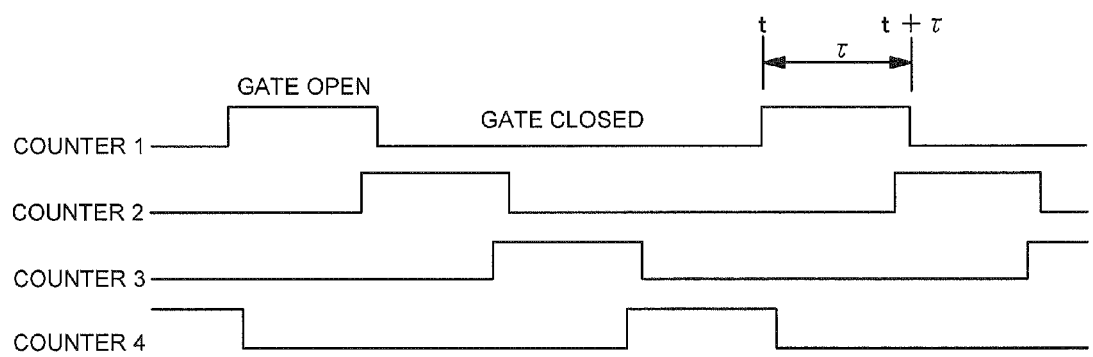
FIG. 4 is a timing chart showing open/close of a gate in this embodiment.

More concretely, as shown in FIG. 4, it is so controlled that the gate time (shown by τ in FIG. 4) of each counter 6 becomes equal and the timing (shown by t in FIG. 4) to open each gate is repeated sequentially with a certain time period deviated for each of the counters 6. In addition, the gate time of one counter 6 slightly overlaps the gate time of the next counter 6 so that at least a gate of either one of the counters 6 opens on a constant basis and the pulse number can be counted with considering a dead time that fails monitoring. The pulse number counted by each counter 6 is sent to a selector 10 while the gate of the counter 6 itself is closed and then sent to the correlator 8 sequentially by a counter select signal from the control part 7. In the meantime, the counted number is reset. In this embodiment, the minimum time of the gate time is 10 ns, and the sampling at the maximum 100 MHz can be conducted.

The correlator 8 is a linear type sampling correlator, and obtains the auto-correlation data based on the time series data of the pulse number sent in series at certain intervals from each counter 6 through the selector 10. Concretely, the correlator 8 comprises, as show in FIG. 3, a shift register 81 of multiple channels (N channels), a multiplier 82, an accumulator 83 and a storage memory 84. The correlator 8 multiplies the pulse number data stored while shifting in each channel of the shift register 81 with the latest pulse number data by the use of the multiplier 82, and accumulates the obtained each multiplied data by the use of the accumulator 83 and then stores the accumulated data in the storage memory 84 as the auto-correlation data. The operation timing such as the shift timing of the shift resister 81, the arithmetic timing of the multiplier 82, and the arithmetic timing of the accumulator 83 is controlled by an operation timing signal from the control part 7.

Since an input signal from the counter 6 to the correlator 8 is a digital value as being a photon pulse number, all digital configuration by the use of a discrete circuit or a programmable logic circuit can be established, thereby enabling better suited for downsizing with high reliability and accuracy at low cost.

A function of the calculating part 9 is served by an information processing unit 103 such as a computer to which predetermined software is installed. The calculating part 9 obtains auto-correlation data stored in the storage memory 84 of the correlator 8 after termination of the measurement by the count of "N" times and calculates particle diameter distribution of the sample according to the known predetermined algorithm. A calculated result is displayed on, for example, a display.

Furthermore, a control part body 11 is arranged for the information processing unit 103 by installing software. The control part body 11 outputs an instruction signal automatically or based on an input instruction by an operator, controls the laser power by controlling the light irradiation part 4 and controls the gate time and the gate time timing by controlling the control part 7 by the use of a particle diameter to which the measurement is expected, a flow rate of the sample flowing in the flow cell 2, and a concentration, a color and a refraction factor of the particles as parameters in order to optimize the measurement condition.

For example, the gate time is set with the particle diameter to which the measurement is expected or the flow rate of the sample flowing in the flow cell 2 as the parameter. More concretely, the smaller the particle diameter is or the faster the flow rate is, the smaller the gate time is set. It is a matter of course that the gate time timing is changed in accordance with the gate time.

In addition, since the counter 6 is of limited bits, if the counted number of the photon is too big, an overflow generates. Conversely, if the counted number of the photon is too small, an S/N ratio descends so that the measurement accuracy is degraded. As a result, the laser power and the time period while the gate is open are set so as to enable an appropriate count with the concentration, the color and the refraction factor of the particle set as the parameter. Furthermore, it is also possible to set the time period while the gate is open in accordance with scaling of the particle diameter or a change rate of the particle diameter.

As mentioned, in accordance with the particle diameter distribution measurement device 1 of this embodiment having the above-mentioned arrangement, since multiple multi-bit counters 6 are arranged in parallel, it is possible to count the photon number at a high speed similar to the pulse obtained by the photoelectron multiplier 51 without failing to count, and to measure the diameter of the particle group that flows together with the dispersion media before its environment changes. As a result of this, the particle diameter distribution can be measured with assuming that the state is steady and equilibrium.

In this embodiment, a gate time changing part 104, a gate time judging part 105 and a gate time setting part 106 are further provided.

The gate time changing part 104 changes the gate time a plurality of times in an anterior measurement mode prior to the actual measurement of the particle diameter distribution. The gate time changing part 104 stores, concretely for example, 10 nsec that is the above-mentioned minimum value, 20 nsec that is twice the minimum value, and 40 nsec that is furthermore twice 20 nsec as the multiple set values to set the gate time. In the anterior measurement, the gate time changing part 104 changes the set value raising sequentially from the small value for every anterior measurement.

Figure 5:
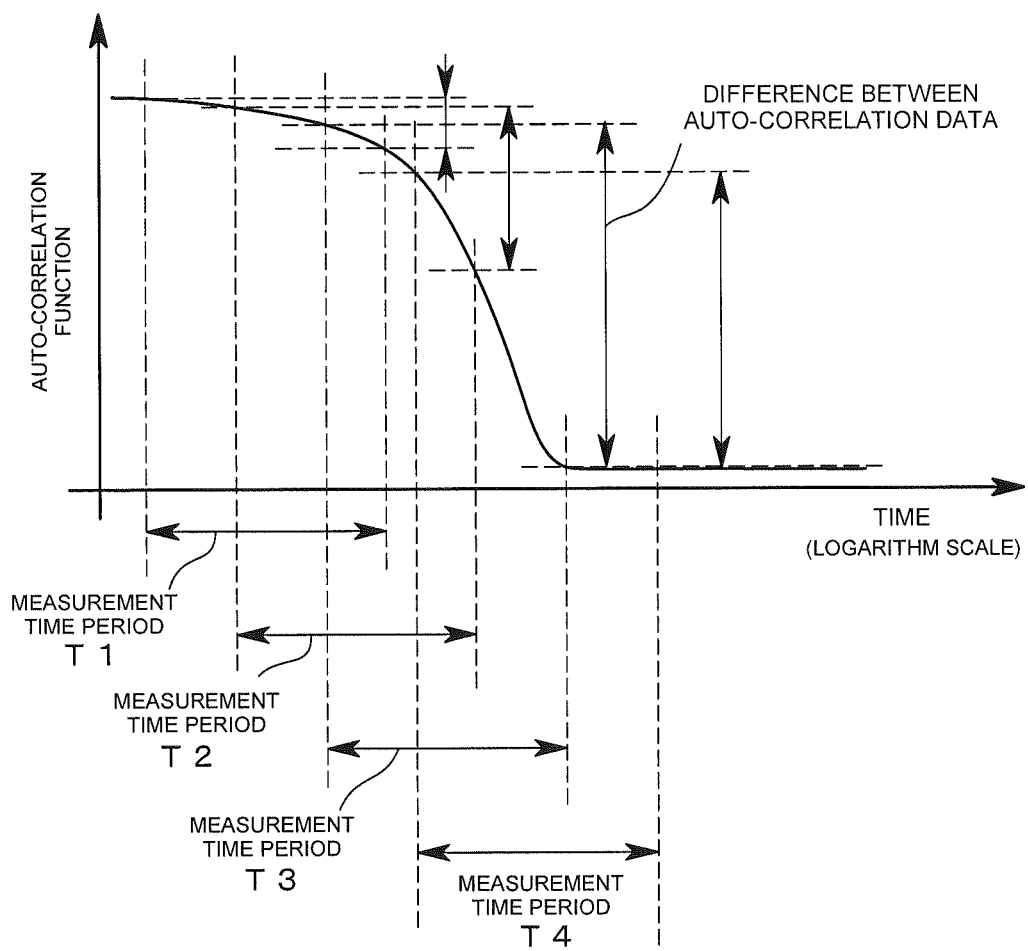
FIG. 5 is a graph showing a relationship between a measurement time and an auto-correlation data in case that gate time is changed in this embodiment.

The gate time judging part 105 judges a recommended value of the gate time that is suitable for the sample in the actual measurement of the particle diameter distribution. The gate time judging part 105 calculates and stores the difference between the maximum value and the minimum value of the auto-correlation data output by the correlator 8 for every anterior measurement wherein the gate time is changed based on the anterior measurement by using one gate time actually conducted after the gate time is changed. Later, the differences between the maximum value and the minimum value of the auto-correlation data stored for every anterior measurement conducted at every time when the gate time is changed are compared at every time when the gate time is changed. As a result of the comparison, the gate time applied to the anterior measurement wherein the difference becomes the maximum is judged as the recommended value. The maximum value and the minimum value of the auto-correlation data correspond to the auto-correlation data at a time of initiation and at a time of termination of the anterior measurement of the measuring time period T1, T2, T3 and T4, as shown in FIG. 5. In case that there are a plurality of values having the identical value among the differences between the maximum value and the minimum value, the gate time judging part 105 judges the gate time corresponding to the shortest measuring time period of the anterior measurement as the recommended value.

The above-mentioned anterior measurement is conducted prior to the actual measurement of the particle diameter distribution by the use of the changed gate time after the gate time is changed by the gate time changing part 104, and obtains the auto-correlation data by the use of the correlator 8. Accordingly, in the anterior measurement, it is not always necessary to calculate the particle diameter distribution of the sample by means of the calculation part 9. In order to obtain the auto-correlation data by the correlator 8, it takes time to shift the time series data of the pulse number counted by the counter 6 to a shift register 81 of N channels. Accordingly in order to conduct a measurement for a single gate time, it requires time almost N times as long as the gate time changed by the gate time changing part 104.

FIG. 5 is a semilogarithmic graph wherein the x-axis is expressed by a logarithmic scale. FIG. 5 shows a change of the measuring time period T1, T2, T3 and T4 of the anterior measurement in case that the gate time is changed. The measuring time period of the anterior measurement in case that the gate time is short is T1. The longer the gate time becomes, the longer the measuring time period becomes such as T2, T3 and T4. In case of the example shown in FIG. 5, the difference of the auto-correlation data becomes the maximum in case of the anterior measurement whose measuring time period is T3.

The gate time setting part 106 sets the gate time judged by the gate time judging part 105 to the counter 6 in case of the actual measurement of the particle diameter distribution.

Figure 6:
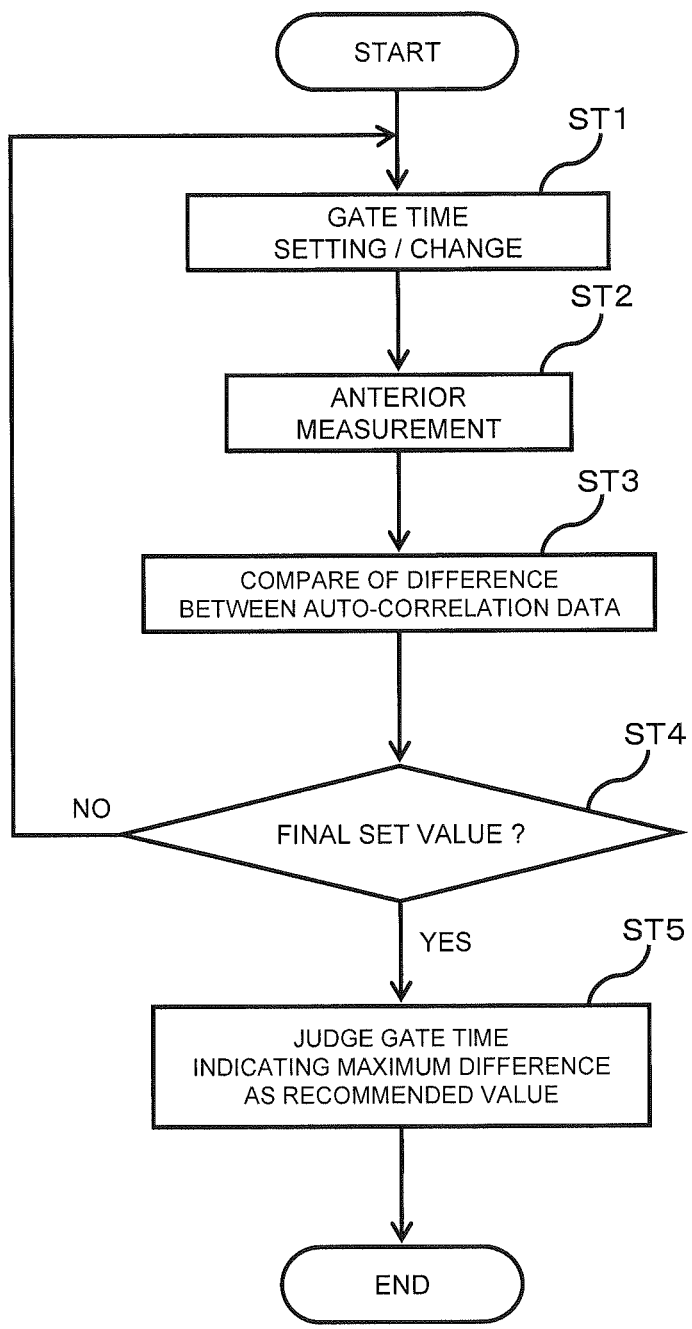
FIG. 6 is a flow chart showing a control movement in this embodiment.

In accordance with this arrangement, the gate time changing part 104 sets the gate time based on the initial set value (Step ST1 in FIG. 6). The anterior measurement (Step ST2 in FIG. 6) is initiated so that the auto-correlation data is output by the correlator 8 and the difference between the maximum value and the minimum value is calculated and stored (Step ST3 in FIG. 6). Later, it is judged whether or not the set value of the gate time is the final set value (Step ST4 in FIG. 6). In case that the set value is not the final set value, the above-mentioned steps are repeated so as to repeatedly conduct the anterior measurement for every time when the gate time is changed and the difference between the maximum value and the minimum value of the auto-correlation data is calculated. Then the gate time is changed a plurality of times. In case that the set value of the gate time is judged to be final, the gate time indicating the maximum difference between the stored maximum value and the stored minimum value is judged to be the recommended value (Step ST5 in FIG. 6).

With the particle diameter distribution measurement device 1 having the above-mentioned arrangement in accordance with this embodiment, the gate time is changed and the difference between the maximum value and the minimum value of the auto-correlation data output by the correlator 8 is compared for every changed gate time, the gate time corresponding to the maximum difference is set as the recommended value, and the recommended value is applied to the gate time of the counter 6 in case of the actual measurement of the particle diameter distribution. As a result of this, it is possible to drastically shorten the time required for adjusting the device in accordance with the preliminary preparation of the measurement of the particle diameter distribution.

In addition, since the recommended gate time is set as the maximum difference between the maximum value and the minimum value of the auto-correlation data obtained by the actual anterior measurement, it is possible to set the gate time tailored to the particle diameter of the sample, namely the sample whose particle diameter is small and attenuation of the auto-correlation data is fast, or the sample whose particle diameter is big and attenuation of the auto-correlation data is slow. As mentioned above, it is possible to automate setting of the gate time that used to depend on manpower for each sample.

Furthermore, it is possible to solve problems such that the accuracy is degraded by setting the gate time long and the gate time appropriate for the sample can not be grasped by setting the gate time short to the auto-correlation data whose attenuation is slow.

The present claimed invention is not limited to the above-mentioned embodiment.

In the above-mentioned embodiment, the device comprising the gate time setting part 106 that sets the gate time by the use of the recommended value is explained, however, the device may display a difference between the recommended value and the other auto-correlation data in case of judgment by the gate time judging part 105, and verify the displayed difference and set the gate time by a user. In this case, it is possible to convey information whether or not an abnormal signal is accidentally detected due to imperceptible contamination detected during the measurement when the scattered light is measured from the sample to the user by displaying a value of a count rate together with the difference.

The present claimed invention is not limited to the above-mentioned embodiment and it is a matter of course that the present claimed invention may be variously modified without departing from a spirit of the invention.

EXPLANATION OF CODES

1 . . . particle diameter distribution measurement device
4 . . . light irradiating part
5 . . . light receiving part
6 . . . counter
8 . . . correlator
9 . . . calculating part
104 . . . gate time changing part
105 . . . gate time judging part
106 . . . gate time setting part

The invention claimed is:

1. A particle diameter distribution measurement device comprising
a light irradiation part that irradiates light on a particle group that moves in a disperse medium,
a light receiving part that receives scattered light emitted from the particle group on which the light is irradiated and that outputs a pulse signal in accordance with a photon number of the received light,
a plurality of multibit counters that are arranged in parallel and each of which has a gate and receives the pulse signal while the gate is open and counts a pulse number,
a correlator that obtains auto-correlation data from time series data of the pulse number obtained sequentially from each of the multibit counters, and
a calculation part that calculates particle diameter distribution of the particle group based on the auto-correlation data obtained from the correlator, and further comprising
a gate time changing part that changes gate time once or a plurality of times and
a gate time judging part that compares mutually, at every time when the gate time is changed, the differences between the maximum value and the minimum value of the auto-correlation data output by the correlator at every time when the gate time is changed by the gate time changing part and judges the gate time corresponding to the maximum difference as a recommended value.

2. The particle diameter distribution measurement device described in claim 1, and further comprising
a gate time setting part that sets the gate time judged by the gate time judging part to the multibit counter.

3. A particle diameter distribution measurement method by making use of the particle diameter distribution measurement device described in claim 1, wherein
the gate time to each multibit counter is changed once or a plurality of times, and
the differences between the maximum value and the minimum value of the auto-correlation data output by the correlator at every time when the gate time is changed are mutually compared at every time when the gate time is changed, and the gate time corresponding to the maximum difference is judged as a recommended value.

\* \* \* \* \*